United States Patent [19]

Sankey et al.

[11] Patent Number: 5,463,112

[45] Date of Patent: Oct. 31, 1995

[54] PEROXYCOMPOUNDS

[75] Inventors: John P. Sankey; William Sanderson, both of Warrington; Graham R. Horne, Rawenstall, all of Great Britain

[73] Assignee: Solvay Interox Limited, Warrington, England

[21] Appl. No.: 976,997

[22] PCT Filed: Jun. 7, 1991

[86] PCT No.: PCT/GB91/00921

§ 371 Date: Feb. 2, 1993

§ 102(e) Date: Feb. 2, 1993

[87] PCT Pub. No.: WO91/18876

PCT Pub. Date: Dec. 12, 1991

[30] Foreign Application Priority Data

Jun. 8, 1990 [GB] United Kingdom .................. 9012876

[51] Int. Cl.⁶ .................. C07C 409/08; C07C 409/42; C01B 15/06
[52] U.S. Cl. .................. 562/2; 562/3; 562/55; 252/186.26; 252/186.42; 252/95
[58] Field of Search .............. 562/2-3, 55; 252/186.26, 252/186.42, 186.38

[56] References Cited

U.S. PATENT DOCUMENTS 3,414,593  12/1968  Robson ........................ 562/2
4,536,313  8/1985   Hignett et al. ................ 252/100
4,704,404  11/1987  Sanderson ..................... 514/568
4,824,591  4/1989   Dyroff et al. ................. 252/94

FOREIGN PATENT DOCUMENTS 0079129  5/1983   European Pat. Off. .
0124968  11/1984  European Pat. Off. .
1041417  9/1966   United Kingdom .

*Primary Examiner*—Gary L. Geist
*Assistant Examiner*—Joseph D. Anthony
*Attorney, Agent, or Firm*—Larson and Taylor

[57] ABSTRACT

This invention concerns novel sulphoperoxyacids having the following generic formula

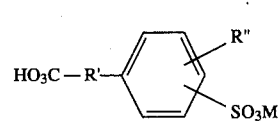

wherein the R', R", and M are as defined in the specification. Bleach compositions and methods of bleaching using such novel sulphoperoxyacids are also taught.

21 Claims, No Drawings

PEROXYCOMPOUNDS

The present invention relates to peroxycompounds and particularly to sulphoperoxyacids, to methods for their preparation, to their selection and use as bleaching agents, to their selection and use as disinfectants and to bleaching, washing or disinfectant compositions containing them.

Peroxycompounds have been incorporated as bleaching agents for many years in bleaching or washing compositions or for their disinfectant properties in disinfecting compositions. In more recent years, there has been a growing interest in the use of peroxyacids for such purposes, in view of their high electropotential which enables them, as a class, to be more effective at lower washing temperatures and at lower molar concentrations than peroxyhydrates and in view of their biocidal effectiveness against a wide spectrum of pathogenic micro-organisms.

The incorporation of the same or a very similar class of peroxyacids containing a range of other substituents in washing or laundering compositions, has been described in a number of patent specifications to leading producers of such compositions, including U.S. Pat. No. 4,005,029 to Procter and Gamble U.S. Pat. No. 4,325,828 to Lever Bros. In such specifications, a formula Y—R—CO$_3$H is disclosed in which Y can represent a number of different substituents including a carboxylic, peroxycarboxylic or sulphonic acid/ salt group. Although this is not always apparent from the disclosures in those specifications, there are differences in effectiveness at bleaching or disinfecting between the various members of such a general class of peroxyacids, depending upon the nature of Y and other substituents and their spatial relationship to the peroxyacid group and to each other. This is confirmed in U.S. Pat. Nos. 4,704,404 and 4,536,313, both to Interox Chemicals Limited, which demonstrated differences performance and/or safety between sulphoperbenzoic acid compounds having the same empirical formula, but differing as to the ortho, meta or pare relationship of the sulpho group and the percarboxylic acid group around the benzene nucleus.

Sulphoperacids are inherently interesting as washing composition components in view of the absence of eutrophying elements from their structure. The aforementioned meta and pare sulphoperbenzoic acid compounds were rather effective against hydrophilic stains, such as red wine, but such stains comprise only a fraction of stains encountered in laundry and it would be desirable to devise other sulphoperacids having an improved effectiveness overall against stains, including less hydrophilic stains.

According to a first aspect of the present invention there are provided as novel compounds sulphoperoxyacids having the following formula (I):

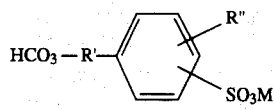

in which R' bonds the percarboxylic acid substituent directly to the benzene nucleus or represents an alkylene group, R" represents at least one alkyl group and the total number of carbon atoms in R'+R" is from 4 to 18, R' and R" optionally forming a cycloalkyl group, and in which the —CO$_3$H and —SO$_3$M substituents are separated by at least 3 carbons linearly, and M represents an alkali metal.

According to a second aspect of the present invention there is provided as bleaching agents a selection sulphoperoxyacids having the formula (I):

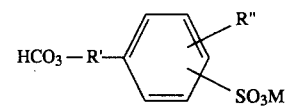

in which R' bonds the percarboxylic acid substituent directly to the benzene nucleus or represents an alkylene group, R" represents at least one alkyl group and the total number of carbon atoms in R'+R" is from 4 to 18, R' and R" optionally forming a cycloalkyl group, and in which the —CO$_3$H and —SO$_3$M substituents are separated by at least 3 carbons linearly and M represents an alkali metal.

According to a third aspect of the present invention there are provided bleaching compositions containing an effective amount of the sulphoperoxyacid of formula (I) described hereinabove in the second aspect of the present invention, and at least one diluent, or detergent builder or surfactant or detergent additive.

According to a fourth aspect of the present invention there is provided a process for washing or bleaching in which laundry or a hard surface is brought into contact with an effective concentration of a sulphoperoxyacid of formula (I) described hereinabove in the second aspect of the present invention.

According to a fifth aspect of the present invention there is provided respectively as disinfectants or sanitising agents, the selection of sulphoperoxyacids of formula (I) described hereinabove in the second aspect of the present invention, in the sixth aspect disinfecting or sanitising compositions containing an effective amount of the said selection of sulphoperoxyacids and in the seventh aspect processes for disinfection or sanitisation employing an effective concentration of the said selection of sulphoperoxyacids.

It will be recognised that the sulpho acid group is the stronger acid, so that the salt is formed of the sulpho acid group in preference to the percarboxylic acid which remains in acid (hydrogen) form unless excess alkali is employed beyond that providing complete neutralisation of the sulpho acid.

The formula for the invention selection of sulphoperoxyacids includes compounds in which the peroxyacid is a direct substituent of the benzene nucleus and compounds in which the peroxyacid is spaced from the benzene nucleus by an alkylene group. It will also be recognised that an important factor contributing to a successful selection of sulphoperacids is the choice of the total number of carbons in the groups R' and R". By limiting the total carbon number of R' plus R" to the range of from 4 to 18, it is possible to obtain sulphoperoxyacids which remain suitably safe and stable, whilst enjoying greater effectiveness against relatively hydrophobic stains. Of course, in those embodiments in which the peroxyacid directly substitutes the benzene nucleus, all the carbons must be provided by the substituent or substituents R", but when R" is carbon-containing, then the number of carbons in R" can be reduced correspondingly.

In those embodiments of the present invention selection of sulphoperacids in which the peroxyacid substituent directly bonds to the benzene nucleus, ie R" is absent, the sulpho group can be present only in the meta or para positions, in order to meet the aforementioned limitation as to minimum spacing of the two groups. In a number of successfully made compounds, substituent R" is a single substituent para to the peracid group, and is accordingly ortho to the sulpho group. In such compounds, R" often contains from 5 to 9 carbon atoms and at least 5 linear carbons. Preferably, R" is linear, but methyl or ethyl substitution is possible. The alkali metal is preferably potassium. Representative sulphoperacids include 3-sulpho- 4-n pentyl-perbenzoic acid, monopotassium salt, and 3 -sulpho-4-n heptyl-perbenzoic acid, monopotassium salt.

In other, and in some ways preferred embodiments of the present invention selection of sulphoperacids, the peracid group is spaced from the benzene nucleus by an alkylene group R' desirably containing at least three linear carbons, and preferably from 4 to 10 linear carbons. The chain of at least 3 linear carbons often comprises the backbone of R'. Such compounds can be made in reasonable yield without recourse to strong organic acids in the manufacturing reaction medium, such as methanesulphonic acid which are rather expensive. The alkylene group R' is preferably linear, although methyl or ethyl branches can be tolerated and as an alternative means of providing within R' a moiety containing at least 3 linear carbons, that moiety may be present as an alkyl side chain, for example in a substituted methylene or dimethylene group, such as n-butyl substituted methylene. The overall limitation on total number of carbons in the substituents R' and R" continues to apply. In a number of effective and convenient examples, the alkylene/peracid substituent —R'—CO₃H is ortho to the sulpho group and in others the relationship is para. The alkyl substituent R" may be methyl, ethyl or a longer alkyl group, but preferably no longer than hexyl. Indeed, there can be more than one alkyl substituent present around the nucleus, such as two. R", or at least one of two R" substituents may conveniently be located ortho to the sulpho group and are especially methyl. Examples of such compounds include 6-(3 -methyl-4-sulpho-phenyl)-perhexanoic acid, monopotassium salt and 6-(3,5-dimethyl-2-sulpho-phenyl)-perhexanoic acid, monopotassium or monosodium salt. In a modification of the foregoing, instead of R" representing two separate alkyl substituents, particularly when they depend from adjacent carbons around the benzene nucleus, and especially when R" contains four carbons, the two substituents may combine to form an alkylene substituent which completes a second ring and especially a six membered ring, fused with the benzene nucleus. The compounds obtained in such a modification, for example 6-(1,2,3,4-tetrahydro-7-sulpho-naphthalene)-perhexanoic acid, monopotassium salt, enjoy similar washing/bleaching performance to the corresponding compounds in which R" represents two alkyl groups.

In a variation of the first aspect of present invention, a further range of aromatic sulphoperacids according to a modification of Formula (I) can be obtained which satisfy Formula (IA), viz

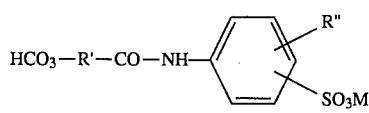

in which R' represents an alkylene group containing at least four carbon atoms, R" represents at least one alkyl group and the total number of carbon atoms in R'+R" is from 10 to 24, and M represents an alkali metal.

Peracids according to Formula (IA) are employed in corresponding variations of the second to fifth aspects of the present invention, namely as bleaching agents, in bleaching compositions, in processes for washing or bleaching or as disinfectants or sanitising agents.

In a modification of the first aspect of the present invention, there is additionally provided a range of aliphatic sulpho peroxyacids satisfying the general formula (II):

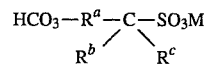

in which $R^a$ is an alkylene group, $R^b$ is an alkyl group and $R^c$ is hydrogen or an alkyl group such that the linear spacing between the sulpho group and the peroxycarboxylic acid group is at least 3 carbons and the total carbon content is from 12 to 24 carbon atoms and M represents an alkali metal.

In corresponding modifications to the other aspects of the present invention, the peroxyacids of formula (II) are substituted for those of formula (I).

$R^a$ preferably contains at least 10 carbon atoms, desirably such that the linear separation between the sulpho and percarboxylic acid groups is at least 10 carbon atoms, and additionally or alternatively is linear rather than branched. $R^a$ is particularly selected within the range of C12 to C18, and especially those which are also linear.

$R^b$ is preferably selected from alkyl groups containing from 1 to 6 carbon atoms and is often methyl, ethyl or propyl, and likewise preferences for $R^c$ when the latter represents an alkyl group. $R^b$ and $R^c$ may be the same as or different from each other. However, preferably, $R^c$ represents hydrogen.

In particularly preferred combinations of substituents, Ra represents a linear polymethylene group containing from 12 to 18 carbons, $R^b$ represents methyl or ethyl and $R^c$ represents hydrogen.

The sulphoperacids of the present invention including those in the modification can be made by a two stage process in which the corresponding and hence precursor sulphocarboxylic acid is peroxidised by reaction with hydrogen peroxide in a suitable strong acidic medium and then neutralised by contact with sufficient alkali metal to neutralise the sulpho group.

In stage 1 of the two stage process, the corresponding carboxylic acid and hydrogen peroxide are brought into contact in a strong mineral acid or organic acid reaction medium at a reaction temperature of below about 50° C., preferably from 5° to 45° C. which is maintained until at least some peroxyacid product has formed. A particularly preferred temperature range for at least part of and preferably at least the final half of the reaction period is from 35° to 45° C. Most conveniently, a product having excellent characteristics can be obtained employing a reaction temperature for an initial period at about ambient temperature, ie around 20° to 25° C. which subsequently is heated to around 35° to 45° C. for the remainder of the reaction period. The reaction period is usually allowed to last for at least 1 hour and often from 1.5 hours to 5 hours.

The amount of hydrogen peroxide to employ is desirably an excess compared with the stoichiometric equimolar ratio to the precursor carboxylic acid, and preferably a mole ratio of at least 2:1 peroxide:carboxylic acid. In many instances the mole ratio is selected in the range of from 3:1 to 5:1 peroxide:carboxylic acid.

Similar reaction procedures are known for making poorly soluble aliphatic peroxyacids, and these can be applied in general to the manufacture of the invention peroxyacids, preferably also taking into account the solubility of the starting materials and the preferred reaction temperatures. In effect, the teaching in such prior publications as Siegel, et al in JOC, vol 27 pp1336–42 in 1961 entitled peroxides IX. New Method for the Direct Preparation of Aromatic and Aliphatic Peroxyacids can be employed, but modified as to the carboxylic acid starting materials. Likewise, various processes described for the production of aliphatic peroxyacids in each of U.S. Pat. No. 2,813,896 (Krimm) U.S. Pat. No. 4,119,660 (Hutchins), U.S. Pat. No. 4,172,086 (Berkowitz), U.S. Pat. No. 4,233,235 (Camden), and U.S. Pat. No. 4,337,213 Marynowski.

Thus, when an organic acid reaction medium for the peroxidation reaction, is employed, it is especially suitably an organic sulphonic acid, such as specifically methane sulphonic acid, which is probably the most readily available lower alkane sulphonic acid. When an inorganic mineral acid reaction medium is employed, it is most preferably sulphuric acid or can alternatively be phosphoric acid. Mixtures of the strong acids, either wholly inorganic or organic and inorganic, can be employed if desired.

It will also be recognised that where the reaction medium comprises a mineral acid, such as sulphuric acid, all or part of it can be premixed with the hydrogen peroxide to form an equilibrium mixture containing for example permonosulphuric acid that can itself perform the peroxidation reaction. Such premixing is beneficial because it separates the exothermic dilution/reaction between hydrogen peroxide and sulphuric acid from the peroxidation reaction, thereby enabling both to be controlled more readily and safely.

In the second stage of the preparation, the solution is at least partially neutralised by the introduction of the alkali metal salt, preferably being a salt of a strong acid such as of sulphuric acid. Particularly acceptable peroxidised products have been obtained by employing a potassium salt. The salt is preferably added so as to introduce substantially the minimum amount of water, such as by adding a saturated or nearly saturated solution of the salt. It can be carried out at the reaction temperature of the first stage, but product precipitation can be assisted by cooling the reaction mixture at the end of the reaction, preferably by at least 10° C., and particularly to a temperature in the approximate range of −5° to 10° C. The product is thereafter separated from the reaction medium employing conventional solid-liquid separation techniques and apparatus, including filtration and centrifugation.

It will be understood that the starting material need not itself be in acid form at the start of the reaction, but can instead be present as an alkali metal salt, with the result that a solid precipitate occurs during the peroxidation stage. Even if the salt of both the sulpho and carboxylic acids is employed, the product is the salt of solely the sulpho group, provided that the reaction mixture remains acidic. Stage 2 encourages recovery of peracid salt from the preparative process.

The attention of readers not skilled in the art of peroxygen chemistry is directed to the potentially hazardous nature of peroxidation reactions and their products, to the need to take appropriate safety precautions at all times and to control the reaction conditions so as to ensure that the reaction mixture never at any time exceeds its SADT, ie its self accelerating decomposition temperature, and to carry out any initial tests on a very small scale.

Notwithstanding the above general warning which is of particular relevance to the formation of many peroxyacids, the isolated peroxyacids of the instant invention are characterised by their generally benign properties, and specifically by their relatively high stability and resistance to decomposition which they combine with an acceptable bleach performance.

The sulpho group in the sulpho carboxylic acid precursors in general can be introduced by sulphonation of the corresponding carboxylic acid compound in accordance with the general principles of sulphonation described in the literature, such as for example using chlorosulphonic acid in an inert organic solvent and reaction conditions like temperature and duration appropriate for the reactivity of the substrate.

A number of the sulphoperacids according to formula (I) herein contain as a substituent of an aromatic nucleus an alkylenepercarboxylic acid group represented by $—(C_5H_{10})—CO_3H$. The precursor carboxylic acid-containing group, it has been found, can be introduced into the precursor compounds very effectively by a further aspect of the instant invention. A process according to this further aspect, is characterised by bringing into contact an mono or polynuclear aromatic hydrocarbon substrate optionally substituted by at least one electron-donating substituent with aluminium chloride and caprolactone in a non-reactive solvent for the caprolactone and maintaining the liquid reaction mixture at a temperature in the range of at least 20° C. often at least 30° C. until at least some of the substrate has been substituted or further substituted by a group of formula $—(C_5H_{10})—CO_2H$.

The alkylation process is suitable for preparing any precursor which after sulphonation and peroxidation is according to formula (I) and contains a group represented by $—(C_5H_{10})—CO_2H$. The aromatic substrate may comprise a hydrocarbon. It may be substituted by one or more electron donating substituents, such as an alkyl group in accordance with formula (I), preferably methyl, or indeed two alkyl substituent may combine to complete a non-aromatic nucleus. In a number of preferred embodiments, the substrate comprises tetralin or a mono, di, or trialkyl substituted benzene or naphthalene.

The solvent for the alkylation process may comprise any aliphatic hydrocarbon or chlorinated hydrocarbon solvent that can provide a liquid composition at the desired reaction temperature or conveniently the solvent comprises the substrate itself, preferably present in an excess over the stoichiometric mole ratio of 1:1 to the caprolactone and more preferably from 1.5:1 to 5:1. Such a mole ratio may be used even if an additional or alternative solvent is used, which latter is preferably present in at least 0.5 parts by volume per volume of substrate, (v/v) and often from 0.5 to 5 parts v/v.

In the alkylation process the aluminium chloride is suitably present in the reaction mixture in a mole ratio to the caprolactone of greater than 1:1 and preferably from 1.2:1 to 2.5:1. It is preferable for the reaction mixture to be formed by first mixing the aluminium chloride with the substrate, preferably under sub-ambient temperatures, such as from 0° to 15° C., and thereafter to introduce the caprolactone, normally epsilon caprolactone. The caprolactone is preferably introduced gradually, either continuously or in small increments over a period of at least 10 minutes and often from 30 minutes to 4 hours. By so doing, it is possible to promote the desired substitution of an alkylcarboxylic acid onto the aromatic nucleus in preference to side reactions involving the caprolactone.

The alkylation process may be conducted at any temperature at which the reaction mixture is liquid, but is preferably carried out at a temperature of from 30° to 50° C. By conducting the reaction at such a comparatively low temperature, it is possible to favour the introduction of a linear group of formula $—(CH_2)_5—CO_2H$ compared with the alternative branched product of formula $—(CHMe)—(CH_2)_3—CO_2H$.

The reaction conditions are often maintained until at least a substantial fraction of the reactant in defieciency has been consumed. In practice, this depends on the substrate and the reaction temperature. The reaction can be allowed to continue for some time after the caprolactone has been introduced. In many instances, the reaction period lasts for from 1.5 to 7 hours, taking into account both the period of caprolactone introduction and subsequent reaction time. Thereafter, the product can be separated out by convention techniques, such as extraction, and/or distillation, or by conventional solid/liquid means, depending on the solubility of the product in the reaction mixture.

The percarboxylic acids according to the instant invention are particulate solids and they can be employed by themselves or can be incorporated as an active bleach component in bleaching or washing compositions containing a range of other ingredients, the selection and amounts of which are at the discretion of the formulator and determine the name for the compositions.

For bleach or bleach additive compositions, the peroxyacid normally comprises from 1 to 80%, and often from 5 to 50%, all %s herein being w/w of the respective composition unless otherwise stated. The remainder, 99 to 20%, comprises a diluent either by itself or together with a minor amount, such as up to 20% in total of optional components such as peroxygen stabilisers, surfactants, etc as indicated subsequently herein. The skilled reader will recognise that many of the diluents described herein as being suitable have hitherto been described as one or other of desensitising diluents or stabilising diluents or exotherm control agents in conjunction with named prior art organic peroxyacids such as DPDDA. Whilst the presence of such diluent compounds may have been necessary to perform that function for those prior art peroxyacids, it is a significant feature of most of the invention peroxyacids that the presence of the same diluents is optional and in practice their selection can be based upon any other desirable feature of those compounds, such as their cheapness or their advantageous washing or detergent-enhancing properties.

The diluent is often a salt selected from anhydrous or hydrated alkali or alkaline earth metal salts of halogen-free acids, and particularly of mineral acids, including salts of sulphuric, and ortho, pyro or hexa-meta phosphoric acids. Preferably, the metal is selected from sodium, potassium and magnesium and in many instances is sodium. Hydrated, partially hydrated or anhydrous sodium sulphate is often chosen in view of its widespread availability, its properties and its cost. It will be recognised, though, that use of a phosphate salt may be preferred in view of its known capabilities of acting as a detergent builder, which can complement especially an unbuilt washing composition.

Other inorganic compounds that are suitable for use as diluents include ortho and meta boric acid and alkali metal salts thereof, and especially sodium salts. Such compounds can buffer solutions of the bleach or additive composition to a pH in the immediate region of the pKa of the peroxyacid and consequently optimise bleach activity. The boric acids have also been used as exotherm control agents in compositions containing peroxyacids such as DPDDA that need to be protected against a tendency to decompose in an otherwise uncontrollable fashion if allowed to reach a quite low threshold temperature, but that property is unnecessary in conjunction with the invention peroxyacids on account of the safe nature of these selected peroxyacids.

Other suitable inorganic diluents include alkali metal carbonates/bicarbonates, aluminium salts of the above-identified mineral acids, and natural or synthetic aluminosilicates and clays, such as zeolites A, X and Y, often in the sodium form, or swelling clays like bentonite. It will be clearly recognised that many of these diluents also enjoy the status of builders in washing compositions, and that each accordingly can perform its known functions such as hardness removal or peptising when employed in bleach compositions. When the bleach composition is intended as a scour, at least a proportion of the diluent and preferably at least half of the diluent comprises abrasive powdered materials, including silica, quartz, marble dust or kieselguhr.

A further and rather different class of suitable inorganic diluents comprises alkai metal or alkaline earth metal halides, especially chlorides and/or bromides and particularly sodium chloride, or sodium bromide or a mixture of the two. By employing this class of diluents as at least a part of the diluents, the composition can generate in solution during use of the composition a halide such as chlorine or bromine which can complement the bleaching/sanitising effect of the invention peroxyacids.

The diluent can comprise a hydrogen peroxide-developing solid persalt, or an inorganic persulphate, preferably in an amount of not more than 50% w/w of the composition. The term "persalt" herein relates primarily to alkali metal perborates, percarbonates and perphosphates, and especially the sodium salts, which generate hydrogen peroxide or the HOO— anion depending on the solution pH, in situ and includes other hydrogen peroxide adducts which can do likewise. Preferred persalts include sodium perborate monohydrate or tetrahydrate and sodium percarbonate. Persalts include adducts with urea and related compounds, adducts with certain aluminosilicates and addition compounds with alkali/alkaline earth metal sulphate/chlorides in specified ratios. It will be recognised that the use of persalts as diluent, such as in at least 10% of the composition, enables the composition to be effective throughout a range of temperatures from ambient up to about 100° C.

In one more specialised type of bleaching compositions, namely effervescent composition, which are often intended primarily for cleansing dentures, but which can also be employed for many other purposes, the diluent for the invention peroxyacids preferably contains a gas generating system and if necessary a pH regulator. Compounds that are suitable for gas generating systems and as pH regulators are well known in conjunction with existing peroxyacids, and are described in EP-A-0 133 354 in the name of Interox Chemicals Limited. The gas generating system often provides from 10 to 50% and comprises either a carbon dioxide generating combination of an alkali metal carbonate or bicarbonate with a solid water-soluble acid, and especially an organic acid selected from tartaric, citric, lactic, succinic, glutaric, maleic, fumaric and malonic acids, preferably in an equivalent mole ratio of from 1.5:1 to 1:1.5 and especially at about 1:1, or an oxygen-generating compound known as anhydrous sodium perborate, $NaBO_3$. The pH regulator often comprises 5 to 40% of the composition. To provide acidic conditions, it can comprise one or more of the aforementioned organic acids in an appropriate excess amount, or sulphamic acid or alkali metal bisulphates, and to provide alkaline conditions, it can comprise alkali metal silicates or excess carbonate/bicarbonates. Selection of the percarboxylic salt form can be advantageous in such compositions.

In the main, the foregoing diluents have been inorganic. However, the invention peroxyacids can be diluted, if desired, with a range of organic substances, including hydrocarbon waxes, alkyl C1 to C6 esters of aromatic mono or di carboxylic acids, solid starches, gelatines and dextrins.

The bleach compositions can also contain, as indicated before, minor components such as peroxyacid stabilisers. The breadth of compounds suitable for this purpose is well-known in this art. These are often organic chelating compounds that sequester metal ions in solution, particularly most transition metal ions, which would promote decomposition of any peroxygen compounds therein, and many suitable ones being classified in the literature as carboxylic acid, hydroxycarboxylic or aminocarboxylic acid complexing agents or as organic amino- or hydroxy-polyphosphonic acid complexing agents, either in acid or soluble salt forms. Representative stabilisers expressed in acid form include picolinic acid, dipicolinic acid, quinolinic acid, gluconic acid, hydroxyethylene di phosphonic acid, and any compound satisfying the general formula:

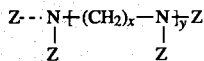

in which Z represents either $-CH_2-CO_2H$ or $-CH_2-PO_3H_2$, x represents an integer selected from 1 to 6, and preferably is 2, and y represents an integer selected from 0, 1, 2 or 3. Within this general formula especially preferred stabilisers include ethylenedia mine tetra acetic acid (EDTA), ethylenediamine tetrakis (methylenephosphonic acid) (EDTMP), and diethylenetriamine pentakis (methylenephosphonic acid) (DTPMP). A further and particularly effective stabiliser comprises cyclohexane-1,2-diamine tetrakis (methylenephosphonic acid), CDTMP. The amount of stabiliser is often up to 5% of the composition and in many instances is selected in the range of from 0.05 to 1%.

If present at all, a surfactant is present in bleaching compositions only in a small amount, such as up to about 5% and in many instances from 0.1 to 2% of the composition. It can be selected from the surfactants described subsequently herein for washing compositions.

The invention bleaching compositions will often comprise particulate mixtures, which can be stored loosely in conventional waxed boxes, or alternatively be enclosed in rupturable pouches or in porous or perforated bags or sacs through which bleaching solution can penetrate. Such mixtures can be obtained by dry blending the particulate components, or they can be aggregated using conventional agglomeration or granulation techniques, using water or a removable solvent and optionally a granulating aid hitherto described for use with an organic peroxyacid. Alternatively, by virtue of their demonstrated ability to withstand pressure, all but the least resistant invention peroxyacids can be compressed in tablets and like bodies. Accordingly, it is possible to provide peroxyacids in easy to use predetermined dosage levels for the end user.

The bleaching compositions can be used by themselves, such as in a pre-wash bleach or a post-wash rinsing stage of a multistage laundry process or in cleansing both absorbent or non-absorbent (sometimes called "hard") surfaces. They are more usually employed in conjunction with a washing composition based upon surfactants. Naturally, surfactants and optional ingredients of washing compositions can be premixed with the instant bleaching compositions to form bleach-containing washing compositions.

Washing compositions according to this further aspect of the present invention contain from 0.5 to 50% of the invention peroxyacids, from 1 to 90% surfactant, from 0 to 90% detergent builder, from 0 to 90% diluent and from 0 to 20% minor components. It will be recognised that the composition of the invention washing compositions range within very broad limits. Choice of the peroxyacid in acid form can be beneficial herein, in order to minimise or avoid spotting problems that can occur if excessive local concentrations of active bleach should be allowed to remain in contact with a dyed fabric for too long.

In many preferred compositions according to the present invention, one or more of the composition components are selected within the following narrower bands:

| | |
|---|---|
| Invention peroxyacid | 1 to 25%, particularly 2 to 10% |
| surfactant | 2 to 40%, particularly 5 to 25% |
| builder | 1 to 60%, particularly 5 to 40% |
| diluent | 1 to 70%, particularly 5 to 50% |
| minor components | 1 to 10% in total. |

The surfactants for incorporation in solid compositions of the present invention can be selected from particulate or flaky anionic, cationic, non-ionic, zwitterionic, amphoteric and ampholytic surfactants and can be either natural soaps or synthetic. A number of suitable surfactants are described in chapter 2 of Synthetic Detergents by A. Davidsohn and B. M. Milwidsky (6th edition) published in 1978 by George Godwin Ltd and John Wiley & Sons, incorporated herein by reference. Without limiting to these surfactants, representative sub-classes of anionic surfactants are carboxylic acid soaps, alkyl aryl sulphonates, olefin sulphonates, linear alkane sulphonates, hydroxy-alkane sulphonates, long chain and OXO alcohol sulphates, sulphated glycerides, sulphated ethers, sulpho-succinates, alkane sulphonates, phosphate esters, sucrose esters and anionic fluorosurfactants; representative classes of cationic surfactants include quaternary ammonium or quaternary pyridinium salts containing at least one hydrophobic alkyl or aralkyl group, representative classes of nonionic surfactants include condensates of a long chain alkanol with either polyethylene oxides or with phenols, or condensates of long chain carboxylic acids or amines or amides with polyethylene oxide, and related compounds in which the long chain moiety is condensed with an aliphatic polypol such as sorbitol or condensation products of ethylene and propylene oxides or fatty acid alkanolamides and fatty acid amine oxides; representative classes of amphoteric/zwitterionic surfactants include sulphonium and phophonium surfactants, optionally substituted by an anionic solubilising group. The proportion of surfactant, expressed as a fraction of all the surfactant present is often from ⅔oths to ⁹⁄₁₀ths anionic, from 0 to ⁶⁄₁₀ths nonionic, and from 0 to ³⁄₁₀ths for the other surfactants.

It will be recognised by the knowledgable reader that many of the classes of diluent described herein above for use in bleaching compositions are also called detergent builders. These include specifically alkali metal phosphates, particularly tripolyphosphate but also tetrapyrophosphate and hexametaphosphate, especially the sodium salt of each, alkali metal, preferably, sodium carbonate, alkali metal, preferably, sodium borates, and the zeolites A, X and Y and clays like bentonite. Amongst organic compounds, the chelating compounds which were described herein as peroxygen stabilisers can also function as detergent builders. Particularly preferred chelating builders include nitrilotrisodium trisacetate (NTA), EDTA, EDTMP and DTPMP. Such chelating builders can be employed in a relatively small amount as an augmenting builder and peroxygen stabiliser, such as of 1 to 10%, or in cooperative partnership of equals in conjunction with a phosphatic or zeolitic or clay builder, the weight ratio of chelating to inorganic builders often being from 4:1 to 1:4, or alternatively they can be employed as the principal builder in amounts of up to 40% such as in the range of 5 to 30% of the washing composition.

The other types of compounds that have been indicated to be suitable for use as diluents in a bleaching composition, can also be employed for the same primary purpose and secondary purpose, if any, in washing compositions, although it will be recognised that the presence of an effervescent system in washing compositions is comparatively rare. For the avoidance of doubt, persalts can be incorporated in the instant washing compositions, preferably in an amount of up to 30%, such as 1 to 20%, and sometimes in a weight ratio to the invention peroxyacids of from 5:1 to 1:5. A diluent commonly present in these washing compositions is sodium sulphate, often from 5 to 50%, because it also functions as a processing aid. The previously mentioned salts that enable a halogen to be generated in situ can likewise be present in the washing compositions, which can then enjoy the alternative name of sanitising compositions.

The washing compositions can contain a number of optional components, sometimes alternatively called auxiliary agents. These agents which can each individually be included include soil anti redeposition agents (SARDs), dye transfer inhibitors, optical brightening agents (OBAs), stabilisers, corrosion inhibitors, bactericides, dyes, perfumes, foam enhancers, foam inhibitors, pH regulators and absorbents. The amount for each auxiliary agent is often selected in the range of 0.02 to 0.2% for dyes and perfumes and from 0.1 to 2% for each of the other auxiliary agents. It is preferable to select auxiliary agents which are known not to interact with peroxygen compounds during storage or to coat the agent with or incorporate the agent in a known fashion within a matrix of a dispersible material such as a wax or the many other film-forming substances proposed in the literature for separating organic peroxygen compounds from co-components, e.g. in EP-B-00 27 693 to Interox Chemicals Limited. Such substances can also function as granulating aids (binders), if the invention compositions are granulated or agglomerated. Examples of suitable SARDs include carboxymethyl cellulose particularly the sodium salt, polyvinylpyrrolidone and examples of OBAs include derivatives of diaminostilbene sulphonic acid and 1,3-diaryl-2-pyrazolines and aminocoumarins.

The invention washing compositions can be dampened or dissolved in a little water for cleaning and disinfecting non-adsorbent surfaces such as walls, floors, work surfaces, vessels, baths, sinks and sanitaryware of metal, plastics, ceramics or glass, wood and rubber.

One of the main intended uses of the washing compositions is to cleanse and indeed also disinfect soiled adsorbent materials such as household laundry items or other articles made especially from cotton, rayon, flax or wool or man-made fibres such as polyesters or polyamides. The cleansing processes can be carried out at ambient temperature or at elevated temperature up to the boiling temperature of the washing solution. The more preferred washing temperature for laundry is from 30° to 60° C. In laundering, it is desirable to introduce sufficient washing composition and/or bleach additive composition to provide at least 5 ppm avox from the peroxyacid, and often from 10 to 50 ppm avox, ppm indicating parts per million by weight and avox indicating available oxygen. This can often be provided by the introduction of the invention washing composition selected in the range of 1 to 25 gpl, or bleach additive composition selected in the range of from 0.5 to 10 gpl, the selection taking into account the concentration of peroxyacid therein. The presence of persalts in the wash can supplement avox levels, for example by amounts of from 10 to 100 ppm avox. In use, depending upon whether and the extent to which alkaline materials, especially builders, are present in the composition itself or in any accompanying washing composition, the compositions generate upon dissolution either a mildly acidic through to especially a mildly alkaline pH. It is preferred to generate a pH of from 7.5 to 9.5 and especially around pH 8 to about 9.0 to optimise bleaching/washing performance from the peroxyacid.

For use in disinfection, it is often preferable to employ an invention peroxyacid concentration of up to 200 ppm avox and in many instances from 25 to 100 ppm avox. It is also suitable to employ a solution spanning neutrality, from mildly acidic, such as at least pH 4 up to mildly alkaline, such as pH 9. In order to attain a pH in such a range, the choice of builders/diluents is so made as to avoid highly alkaline materials and instead select those that generate mild acidity or alkaninity such as sodium dihydrogen phosphate.

The washing processes for laundry can be carried out in currently available equipment. Washing times typically range from about 10 minutes to 30 minutes. Hand washing and extended steeping using solutions of the invention compositions can alternatively or additionally be used. Specialist variations of the invention compositions, such as those intended for nappy sanitisation/cleansing or for denture cleansing are preferably used in the accepted manner for prior art compositions, for example steeping a soiled nappy in a warm peracid-containing solution for several hours before washing it using laundry techniques.

Having described the invention in general terms, specific embodiments will now be described more fully by way of example only.

Example 1

Preparation of 3-sulpho-4-heptylperoxybenzoic acid, potassium salt (HSPBA).

3-sulpho-4-heptyl benzoic acid, sodium salt (10 g) was stirred into methane sulphonic acid (100 g) at ambient temperature, about 22° C., and then concentrated hydrogen peroxide solution, nominally 85% $H_2O_2$ w/w, 6 g, was gradually introduced over a period of about 15 minutes, resulting in a small rise in temperature. The reaction mixture was heated to 40° C. and stirred for a period of 2 hours, then cooled rapidly to about 0° C. and quenched by introduction of a saturated solution of potassium sulphate, 100 ml. The resultant mixture was cooled to 0° C., and the precipitate having a gelatinous-appearance was isolated by filtration. The filter-cake was re-slurried with further saturated potassium sulphate solution, refiltered and dried. The resulting product had a w/w measured available oxygen content (abbreviated herein to "avox") of 4.16% compared with a theoretical avox of 4.52% for the potassium salt, giving a purity of about 91% for the HSPBA product.

Example 2

Preparation of 3-sulpho-4-pentylperoxybenzoic acid, potassium salt (PSPBA).

Example 1 was repeated, but on half the scale and employing 3-sulpho-4-pentyl-benzoic acid, sodium salt. The resultant product had an avox of 4.23% w/w compared with a theoretical avox for the product of 4.7% indicating a purity of about 86% PSPBA.

Example 3

Preparation of 6-(3-methyl-2-sulpho-phenyl)-peroxyhexanoic acid, potassium salt, (STPHA).

6-(3-methyl-2-sulpho-phenyl)-hexanoic acid, disodium salt, 5 g, was introduced over a period of 15 minutes into an equilibrated solution, 30 g, made by premixing concentrated hydrogen peroxide nominally 85% with concentrated sulphuric acid, in a mole ratio of $H_2O_2:SO_3$ of 1:3.2. The reaction mixture was stirred for a further 3 hours and maintained throughout at approximately 20° C. The mixture eventually contained a fine yellowish suspension. The mixture was then quenched by introduction of saturated potassium sulphate solution, 30 ml, and cooled to 1° C. The precipitate was filtered off, re-slurried with further saturated potassium sulphate solution, refiltered and dried. The solid isolate had an avox content of 3.73% w/w compared with a theoretical avox for the potassium salt of 4.48%, indicating a purity of about 83% STPHA.

Example 4

Preparation of 6-(3,5-dimethyl-2-sulpho-phenyl)-perhexanoic acid, potassium salt, (SXPHA).

In this Example, a solution of 6-(3,5-dimethyl-2-sulpho-phenyl)-hexanoic acid, monopotassium salt (4 g) in dichloromethane, 150 ml, was heated with stirring to 30° C. Concentrated hydrogen peroxide solution, 4.14 g, 85% w/w, i.e. 3.5 moles per mole of substituted hexanoic acid, was introduced slowly but continuously throughout a period of about 20 minutes. The solution was heated to reflux temperature for the dichloromethane, ie about 40° C. and allowed to reflux for about 3 hours. The reaction mixture was cooled in an ice bath to below 5° C. and then poured onto crushed ice, 20 g. A little ice water which was used to wash out the flask was combined with the iced mixture and stirred for about 15 minutes. The mixture was filtered and the cake washed, first with filtered mother liquor and then with small volumes of iced water until the pH of the filtrate was about pH 3.0. The filter cake was then air dried. The resultant product, 4.2 g, had an avox of 4.47% compared with a theoretical avox of 4.51% indicating a purity of over 99% SXPHA.

Analysis of the products of Examples 1 to 4 The avox was measured by a standard technique in which a measured weight of sample was dissolved in acetic acid, if necessary augmented with dichloromethane to ensure that the sample is completely dissolved. The sample is then allowed to react in the dark, for 10 minutes with a measured amount of sodium iodide stabilised with sodium carbonate, in the presence of ferric chloride, and the resultant solution is titrated against standardised sodium thiosulphate solution until the pale yellow coloured solution becomes colourless. The result is compared with a corresponding titration against a blank solution, and from the difference the avox is calculated.

All the isolated peroxyacid products were analysed by conventional IR and NMR techniques. The IR traces exhibited a significant peak in the region of 1720 to 1760 cm-1 upwardly shifted from the corresponding peak of about 1700 cm-1 in the corresponding non-peroxidised carboxylic acid starting material confirming the presence of a percarboxylic acid substituent obtained from a carboxylic acid substituent. The resulant products and starting materials each exhibited two significant peaks in the region of 1140 to 1230 cm-1 and two in the region of 1020 to 1060 cm-1 which is indicative of the presence of a sulpho substituent.

Proton NMR and where necessary carbon 13 NMR were employed to elucidate the carbon structure. The number of peaks in the region of about 7 to 7.8 chemical shift for proton NMR indicates the number of unsubstituted carbon around the benzene nucleus and the number of peaks and their complexity in the region of from about 1.2 to 2.6 chemical shift indicate the number of aliphatic carbons and the number of appendent hydrogens. For SXPHA, the lack of symmetry in the positioning of the substituents was deducible because there were two distinct aromatic proton shifts visible, so that the sulpho group was ortho to the peroxyalkyl substituent instead of para to it. For PSPHA, the fact that the sulpho group was para to the peroxyalkyl substituent was confirmed by carbon NMR, because a doublet at J=3.9 Hz indicates that the methyl substituent is adjacent to a single ortho hydrogen and not to two.

Peroxyacid safety, stability and performance The peroxyacids were subjected to a number of tests to determine their effectiveness as a bleach, their hazard rating and their storage stability. The compounds were also compared in these tests with a reference peroxyacid, potassium sulphoperbenzoic acid, the closest peroxyacid known in the published literature. The tests were carried out as follows:

Storage stability

In this test, weighed samples of the peroxyacid are individually sealed in glass phials with a bubbler cap that permits excess internal pressure to vent to atmosphere, and stored in a dark chamber that is thermostatically controlled to 32° C. The avox of the peroxyacid is measured shortly after its preparation ie A0 and after predetermined storage intervals, As, the measurement being made on entire individual samples. The stability results of stored samples are As/A0, quoted as a percentage, the higher the better. Avox is measured by the method described hereinabove.

It will be recognised that the storage stability of the peroxyacid by itself is an extremely important characteristic of a peroxyacid, not only because the compound is likely to be stored in that way before it is incorporated in specific compositions, but also because this represents the intrinsic stability of the compound, the maximum attainable even if the remaining components of compositions containing it are benign.

A + indicates that the compound is according to the invention whereas a − indicates that it is present by way of comparison.

TABLE 2

| Compound | Proportion of avox remaining after 5 weeks |
| --- | --- |
| − KSPBA | 100 |
| + HSPEA | 99 |
| + PSPEA | 100 |
| + STPHA | 92 |
| + SXPHA | 98 (12 weeks) |

It will be observed that the invention compounds are demonstrating an acceptable or most acceptable level of stability.

Hazard Rating

Two tests are described below to demonstrate the hazard rating of the peroxyacid. They are respectively an impact sensitivity test and a pressure-time test.

In the impact sensitivity test, a weight (in kg) is dropped once from a measured height (in cm) onto a fresh sample of the peroxyacid held in the anvil. The sample is thus subjected to an impact, normally expressed as kg-cm (1 kg-cm= $9.8 \times 10^{-2}$ J) that is proportionate to the height and weight. The test is carried out many times at each impact strength, and is observed to see whether the sample responds, by charring, emitting smoke or at worst undergoing a minor explosion. The tests start at a low impact strength and are continued at increasing strenghts until the limiting result is obtained, being the earlier of either 50% of the tests at that impact strength give positive results or a figure of 500 kg-cm is reached, which past experience indicates to represent a non-impact-sensitive product. The limiting result in kg-cm is shown in Tables summarising the results, the higher the better.

In the pressure-time test, 2 g samples of the test material is placed inside an 18 ml steel bomb, and its decomposition initiated. The consequential rise in pressure is monitored and plotted or displayed against elapsed time, expressed in milliseconds. In Table 3, the time is given for the pressure in the bomb generated by the sample to increase from 100 to 300 psi, ie from $6.895 \times 10^5$ Pa to $2.068 \times 10^6$ Pa, the longer the better. The symbol oo indicates that a pressure of 300 psi was not reached, ie a period of infinite duration. By way of interpretation, a time of less than 30 milliseconds indicates that the material is potentially explosive, a time of 30 to 60 milliseconds indicates that it is marginally explosive, and to allow a safety margin, it is preferred to be around 100 milliseconds or longer.

TABLE 3

| | Hazards rating results | |
|---|---|---|
| Compound | Impact kg-cm | p-t msec |
| − KSPBA | >500 | ∞ |
| + HSPBA | >500 | ∞ |
| + PSPEA | >500 | ∞ |
| + STPHA | >500 | ∞ |
| + SXPHA | >500 | ∞ |

From the foregoing Table it will be seen that the products of the instant invention have retained their excellent resistance to impact and thermal shock.

Bleach/Washing Evaluation

The effectiveness of the invention and comparison peroxyacids was tested by washing swatches of cotton cloth that had been preimpregnated in a standard manner with one of four representative stains, tea, red wine, grass and blue polish. The evaluations were carried out in a laboratory scale washing machine, a "Tergotometer" (Trade Mark) available from the US Testing Corporation, under identical standardised conditions. The washing solution comprised local Cheshire tap water, hardness of about 160 to 180 ppm hardness as calcium carbonate, in which was dissolved a peroxyacid-free washing composition at 6.5 g/l. Composition DBNSPA used in all trials had the approximate analysis:

| Composition Component | DBNSPA % w/w |
|---|---|
| Anionic surfactant | 9 |
| Nonionic surfactant | 8 |
| Other organics | 1 |
| Sodium carbonate | 3 |
| Sodium sulphate | 19 |
| Sodium phosphate | 36 |
| Sodium silicate | 10 |
| Sodium Borate | 4 |
| Water | balance |

A weighed amount of peroxyacid was introduced into the washing solution to provide a peracid avox of 25 ppm therein, assuming total dissolution. This corresponds to a molar concentration of $1.56 \times 10^{-3}$M monoperoxyacid. The washing solution was kept at pH9 and at 40° C. during the washing period of 20 minutes. The swatches were then rinsed and dried and the extent of stain removal was determined by comparing the reflectance of the washed cloth, Rw, with that of the pre-washed, stained cloth, Rs, and that of the unstained cloth, Ru. The measurements were obtained using an Instrumental Colour System "Micromatch" (Trade Mark) reflectance spectrophotomer equipped with a Xenon lamp filtered through a D65 conversion filter to approximate to CIE artificial daylight. Stain Removal, expressed as a percentage, % SR, was calculated using the formula:

% SR=100×[Rw−Rs]/[Ru−Rs]

It will be recognised that by demonstrating the washing capability of the peroxyacids in this way, the tests using the invention peroxyacids are in themselves Examples of washing processes according to other aspects of the present invention. Similarly, since the swatches had not been stored in sterile conditions before being washed, the washing procedure will act simultaneously to disinfect them.

The results quoted below are the mean of two evaluations. Comparative results on the same stained cloths using the washing composition by itself, ie without any added peracid, are designated "base".

TABLE 4

| | | % Stain Removal | | | | |
|---|---|---|---|---|---|---|
| Ex/Comp No | Peracid employed | Red Wine | Grass | Tea | Blue Polish | Average Removal |
| First series | | | | | | 3 stains |
| C5 | base | 64 | 51 | 46 | — | 54 |
| C6 | KSPBA | 83 | 63 | 69 | — | 72 |
| 7 | HSPBA | 82 | 74 | 69 | — | 75 |
| 8 | STPHA | 84 | 68 | 76 | — | 76 |
| Second series | | | | | | 4 stains |
| C9 | KSPEA | 85 | 86 | 74 | 52 | 74 |
| 10 | SXPHA | 92 | 87 | 79 | 53 | 78 |

From Table 4, it can be seen that the invention peracids are very effective bleaching agent at hand-hot washing temperatures, and in particular demonstrate a good or improved performance on average against a range of conventional stains that includes both the comparatively hydrophobic stains like grass as well as the the more hydrophilic stains such as red wine or tea.

Bleach Additive Formulations

Representative formulations are made by dry mixing particulate invention peroxyacid with a premixture of the remaining components. In these and subsequent formulations, the designations STPHA (tq), SXPHA (tq), indicate products each containing approximately 4.5% avox w/w. LAS represents a linear alkyl benzene sulphonate, sodium salt, average alkyl length of C11.5, and OBA represents an optical brightening agent.

TABLE 5

| Example No Particulate Components | 11 % w/w | 12 % w/w | 13 % w/w |
|---|---|---|---|
| STPHA (tq) | — | 34.8 | — |
| SXPHA (tq) | 9.1 | — | 73.4 |

TABLE 5-continued

| Example No<br>Particulate Components | 11<br>% w/w | 12<br>% w/w | 13<br>% w/w |
|---|---|---|---|
| LAS | 3 | 4 | 5 |
| OBA + chelate | 0.2 | 0.2 | 0.2 |
| Sodium sulphate | 87.7 | 61.0 | 21.4 |

Dosing of formulations 11, 12 and 13 each at 1.25 gpl provides respectively avox concentrations in solution of approximately 5 ppm, 20 ppm and 40 ppm. Solid bleach additive compositions containing a pH buffer to lower the solution pH closer to about pH 8.5, and hence improve stain removal are made by replacing about 10% w/w of the sodium sulphate by boric acid.

Sanitizer Formulations

Representative formulations are made by dry mixing the specified invention peroxyacids with the other components specified in Table 6.

TABLE 6

| Example No<br>Particulate Components | 14<br>% w/w | 15<br>% w/w | 16<br>% w/w |
|---|---|---|---|
| STPHA (tq) | — | 10.8 | — |
| SXPHA (tq) | 6.6 | — | 15.7 |
| LAS | 9.0 | 7.0 | 5.0 |
| Sodium carbonate | 20.0 | 23.0 | |
| STPP | 10.0 | 10.0 | 10.0 |
| Sodium bicarbonate | | | 26. |
| Sodium chloride | 45.9 | 48.0 | 42.5 |
| Borax | 8.5 | | |
| Organic chelate | | 1.2 | 0.8 |

When the formulations Table 6 are dosed into a nappy (or similar article) sanitising solution in an amount of 5 gpl, the invention peroxyacids provide an avox of respectively 35, 15 and 25 ppm approximately.

Washing Formulations

Representative washing compositions according to the present invention are made by dry mixing the particulate invention peroxyacid with a blend of the other components shown in Table 7. The abbreviations STPP and PBS1 represent respectively sodium tripolyphosphate and sodium perborate monohydrate. The chelating agent is EDTMP, ethylene diamino (tetramethylene phosphonate), Na salt.

Use of Example formulations 17 to 22 at a concentration of 8 gpl in the washing liquor, a typical level for front loading washing machines in Europe, results in peracid avox concentrations of approximately 10, 20, 30, 15, 25, and 35 ppm respectively.

TABLE 7

| Example No<br>Components | 17<br>% w/w | 18<br>% w/w | 19<br>% w/w | 20<br>% w/w | 21<br>% w/w | 22<br>% w/w |
|---|---|---|---|---|---|---|
| BIPTA (tq) | 2.8 | — | 8.1 | — | 6.9 | — |
| SXPHA (tq) | — | 5.4 | — | 4.1 | — | 9.9 |
| LAS | 7.0 | 9.6 | 8.6 | 7.0 | 6.0 | 6.0 |
| Alcohol Ethoxylate | 5.1 | 3.8 | 5.7 | 2.5 | 6.0 | 7.0 |
| STPP | 34.0 | 26.1 | | 40.0 | 30.0 | 30.0 |
| Zeolite A | | | 22.5 | | | |
| Carboxylate builder | | 2.0 | 15.0 | | | |
| Sodium sulphate | 13.9 | 37.0 | 23.2 | 18.0 | 22.9 | 15.3 |

TABLE 7-continued

| Example No<br>Components | 17<br>% w/w | 18<br>% w/w | 19<br>% w/w | 20<br>% w/w | 21<br>% w/w | 22<br>% w/w |
|---|---|---|---|---|---|---|
| Sodium silicate | 14.0 | 6.7 | 7.6 | 6.5 | 5.0 | 5.0 |
| Soap | 6.5 | | | 3.0 | 3.0 | 2.0 |
| Buffer (boric acid) | 10.0 | | | 10.0 | 10.0 | 10.0 |
| PBS1 | | | | | | 9.0 |
| CMC | 1.0 | 1.0 | 1.0 | 1.0 | 1.0 | 1.0 |
| Minors (Chelate +<br>OBA + Perfume etc) | 0.4 | 0.4 | 0.4 | 0.6 | 0.3 | 0.5 |
| Water | | | balance | | | |

Dilute Disinfectant Compositions

Particulate disinfectant compositions are made by dry mixing the components specified in Table 8.

TABLE 8

| Example No<br>Particulate Components | 23<br>% w/w | 24<br>% w/w | 25<br>% w/w |
|---|---|---|---|
| STPHA (tq) | — | 11.1 | — |
| SXPHA (tq) | 6.2 | — | 15. |
| Sodium dihydrogen phosphate | 10.0 | 10.0 | 10.0 |
| Boric acid | 5.0 | 5.0 | 5.0 |
| Corrosion Inhibitor | 1.0 | 1.0 | 1.0 |
| Perfume | 0.5 | 0.5 | 0.5 |
| Sodium sulphate | 77.3 | 72.4 | 67. |

When these formulations are employed at a dose level of 1 glp in an aqueous medium requiring disinfection, the concentration of avox therein is respectively 3, 5 or 7 ppm.

Disintegrating Tablet Compositions—Suitable for Dentures

Representative compositions of this type are made by dry mixing the components given in Table 9 below, and then subjecting them to compression in the mould of a tabletting machine to make tablet weighing about 4 g. The polyethyleneglycol binder av mol weight 6000 is designated PEG 6000, the disintegrant was a cross linked polyvinylpyrrolidone available under the Trademark POLYPLASDONE XL and the lubricant was sodium lauryl sulphate.

TABLE 9

| Example No<br>Particulate Components | 26<br>% w/w | 27<br>% w/w | 28<br>% w/w |
|---|---|---|---|
| STPHA (tq) | 9.2 | — | 14.0 |
| SXPHA (tq) | — | 11.6 | — |
| Succinic acid | 25.2 | 15.0 | 15.0 |
| Sodium Bicarbonate | | 25.5 | 40.0 |
| Sodium Carbonate | 10.0 | | |
| PEG 6000 (binder) | 6.0 | 6.0 | 6.0 |
| PVP disintegrant | 1.0 | 1.0 | 1.0 |
| Lubricant | 0.2 | 0.2 | 0.2 |
| Sodium sulphate | 48.4 | 40.7 | 23.8 |

When one tablet of composition 26, 27 or 28 is introduced into water it generates respectively 17, 21.5 or 25.6 mg avox.

Similar formulations are made containing the other exemplified invention peroxyacids, HSPBA or PSPBA by substituting the corresponding amount of each, for either SXPHA or STPHA, based on their avox contents of respectively 4.5% and 4.7% w/w and adjusting the sodium sulphate content appropriately in Examples 11 to 19 and 23 to 28, and adjusting the sodium chloride content appropriately in Examples 20 to 22.

Examples 29 to 31

In these Examples, the storage stability of invention peracid SXPHA was tested in representative particulate heavy duty detergent compositions, containing respectively as the principal builder in Ex 29 sodium tripolyphosphate, in Ex 30 containing zeolite A and in Ex 31 a compact heavy duty composition also containing zeolite A as the principal builder. Each composition was obtained by mixing 6.5 g of the peracid-free detergent composition with 0.56 g of the peracid. The mixtures were stored at 32° C. in plastic phials having a bubbler cap, and the whole contents of individual phials were analysed after predetermined storage intervals for residual avox by the method described for analysing the products of Examples 1 to 4. The proportion of avox retained, (which means the proportion of peracid which had not decomposed) is given in Table 10 below.

TABLE 10

| Example No. | % Avox retained after storage for (weeks) | | |
|---|---|---|---|
| | 4 | 8 | 12 |
| 29 | 93 | 88 | 92 |
| 30 | 90 | 88 | 92 |
| 31 | 85 | 80 | 84 |

The results summarised in Table 10 confirm that the peracid has an acceptable stability in detergent com[posi-tions, particularly when compared the results of the same tests performed at the same time using a well-known peracid diperoxydodecanedioic acid for which the corresponding 12 week storage figures were only 81%, 41% and 49%.

Example 32
Preparation of 6-(1,2,3,4-tetrahydro-7-sulpho-naphthalene)-perhexanoic acid, monopotassium salt.

In this Example, 6-(1,2,3,4-tetrahydro-7-sulpho-naphtha-lene)-hexanoic acid, monopotassium salt (5 g) was dissolved in dichloromethane 75 ml and methane sulphonic acid (2 g). Concentrated hydrogen peroxide solution (85% w/w, 2.2 g), was slowly introduced with stirring into the mixture, which was heated to reflux for 3 hours. The product was subsequently recovered as in Example 4, and was obtained with a purity of about 96%

Examples 33 and 34

In these Examples, Example 10 was repeated, on a fresh set of stains and employing in Example 34 the product of Example 32, KSTPCA. The washing results are summarised in Table 11.

TABLE 11

| Ex/Comp No | Peracid employed | % Stain Removal | | | | |
|---|---|---|---|---|---|---|
| | | Red Wine | Grass | Tea | Blue Polish | Average Removal |
| 33 | SXPHA | 90 | 87 | 85 | 77 | 85 |
| 34 | KSTPCA | 91 | 88 | 84 | 77 | 85 |

From Table 11, it can be seen that KSTPCA performed similarly to SXPHA, within the accuracy margins of the washing trials.

Examples 35 to 37

Preparation of carboxylic acid precursor

In Examples 35 to 37, a group of formula $—(C_5H_{10})—CO_2H$ was introduced into an alkyl or cycloalkyl-substituted aromatic substrate by reaction with aluminium chloride and caprolactone.

In Example 35, a reaction mixture was obtained by first mixing toluene (40 ml) with anhydrous aluminium chloride (25.67 g, 0.193 mole) over a cold water bath at below about 10° C. and then introducing caprolactone (20 g, 0.175 mole) into the mixture with stirring dropwise over a period of 90 minutes. The bath maintained the reaction mixture at a temperature of about 40° C. When gaseous evolution, HCl, had ceased, the mixture was warmed to 50° C. for a further 2 hours. The product mixture was acidified with an ice/HCl mixture, and extracted into ether. The extract was distilled to yield 10.4 g of melting point 140°–144° C. which on analysis by GLC and proton NMR was ascribed the formula

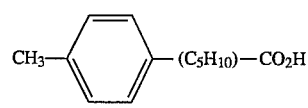

of which 60% (by NMR)/64% by GLC of the alkylene substituent is linear and the remainder comprises $—(CHMe)—(CH_2)_3—CO_2H$ In Example 36, a reaction mixture was obtained by first mixing p-xylene (250 ml) with anhydrous aluminium chloride (153.45 g) over a cold water bath at below about 10° C. and then introducing caprolactone (100.12 g) into the mixture with stirring dropwise over a period of 180 minutes. The bath maintained the reaction mixture at a temperature of about 40° C. The reaction was permitted to continue for a further 2 hours at that temperature. The products were then recovered and analysed as in Example 35. The yield was 163.53 g of product of formula

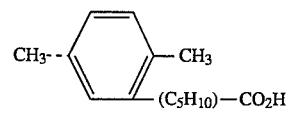

In Example 37, a reaction mixture was obtained by first mixing tetralin (500 g, 3.78 mole) with anhydrous aluminium chloride (630.4 g, 4.72 mole) over a cold water bath at below about 10° C. and then introducing capro lactone (215.6 g, 1.89 mole) into the mixture with stirring dropwise over a period of 180 minutes. The bath maintained the reaction mixture at a temperature of about 30° C. The reaction was permitted to continue for a further 1 hours at about 38° C. The products were then recovered and analysed as in Example 35. An acidic distillation fraction melting at 111° to 114° C. was isolated of formula

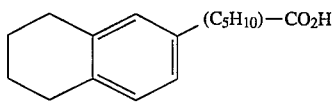

The product was subsequently sulphonated with chlorosulphonic acid in chloroform at about 40° C. to provide the starting material for Example 32.

We claim:
1. As novel compounds sulphoperoxyacids having the following formula (1):

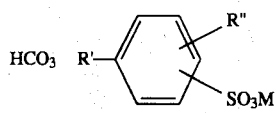

in which R' bonds the percarboxylic acid substituent directly to the benzene nucleus or represents an alkylene group, R" represents at least one alkyl group and the total number of carbon atoms in R'+R" is from 4 to 18, R' and R" optionally forming a cycloalkyl group, and in which the —CO$_3$H and —SO$_3$M substituents are separated by at least 3 carbons linearly, and M represents an alkali metal.

2. A process for washing or bleaching which comprises bringing laundry or a hard surface into contact with an effective concentration of a sulphoperoxyacid of formula (I) in claim 1.

3. Disinfecting or sanitizing composition containing as the disinfectant or sanitizing agent an effective amount of sulphoperoxyacids of formula (I) in claim 1.

4. In disinfection or sanitization processes employing disinfectant or sanitizing agents, the improvement comprising employing as the disinfectant or sanitizing agent an effective concentration of sulphoperoxyacids of formula (I) in claim 1.

5. A compound according to claim 1 wherein the sulpho group is ortho to at least one substituent R".

6. A compound according to claim 1 wherein R" represents two alkyl substituents.

7. A compound according to claim 1 wherein each R" substituent contains from 1 to 6 carbon atoms.

8. A compound according to claim 1 wherein R" is an alkylene substituent completing a six-membered ring fused with the benzene nucleus.

9. A compound according to claim 1 wherein M represents potassium.

10. A compound according to claim 1 wherein R' represents an alkylene group containing at least four carbon atoms, R" represents at least one alkyl group and the total number of carbon atoms in R'+R" is from 10 to 18.

11. A compound according to claim 1 wherein R' is a moiety of from 4 to 10 linear carbon atoms.

12. A compound according to claim 11 wherein the HCO$_3$— substituent is bonded to the terminal carbon atom from the benzene ring of the linear moiety of 4 to 10 carbon atoms.

13. Bleaching composition comprising an effective amount of the sulphoperoxyacid of formula (I) in claim 1 and a diluent.

14. A bleaching composition according to claim 13 wherein the diluent includes at least one compound selected from the group consisting of detergent builder and surfactant.

15. A bleaching composition according to claim 14 wherein R' is a moiety of from 4 to 10 linear carbon atoms.

16. A bleaching composition according to claim 14 wherein the sulpho group is ortho to at least one substituent R".

17. A novel sulphoperoxyacid selected from 3-sulpho-4-n pentyl-perbenzoic acid, monopotassium salt.

18. A novel sulphoperoxyacid selected from 3-sulpho-4-n pentyl-perbenzoic acid, monopotassium salt.

19. A novel sulphoperoxyacid selected from 6-(3-methyl-4-sulpho-phenyl)-perhexanoic acid, monopotassium salt.

20. A novel sulphoperoxyacid selected from 6-(3,5-dimethyl-2-sulpho-phenyl)-perhexanoic acid, monopotassium or monosodium salt.

21. A novel sulphoperoxyacid selected from 6-(1,2,3,4-tetrahydro-7-sulpho-naphthalene)-perhexanoic acid, monopotassium salt.

* * * * *